United States Patent
Banov

(10) Patent No.: US 9,750,813 B2
(45) Date of Patent: *Sep. 5, 2017

(54) USE OF HEPTYL GLUCOSIDE AS SKIN PENETRATION ENHANCER IN TRANSDERMAL PHARMACEUTICAL COMPOSITIONS

(71) Applicant: Daniel Banov, Sugar Land, TX (US)

(72) Inventor: Daniel Banov, Sugar Land, TX (US)

(73) Assignee: Professional Compounding Centers of America (PCCA), Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/682,419

(22) Filed: Apr. 9, 2015

(65) Prior Publication Data

US 2016/0296626 A1    Oct. 13, 2016

(51) Int. Cl.
| | |
|---|---|
| *A61K 31/56* | (2006.01) |
| *A01N 43/00* | (2006.01) |
| *A61K 47/26* | (2006.01) |
| *A61K 31/565* | (2006.01) |
| *A61K 47/14* | (2017.01) |
| *A61K 9/00* | (2006.01) |

(52) U.S. Cl.
CPC ............ *A61K 47/26* (2013.01); *A61K 9/0014* (2013.01); *A61K 31/565* (2013.01); *A61K 47/14* (2013.01)

(58) Field of Classification Search
CPC .... A61K 31/565; A61K 31/575; A61K 31/56; C07J 9/00
See application file for complete search history.

(56) References Cited

U.S. PATENT DOCUMENTS

| | | | |
|---|---|---|---|
| 7,858,607 B2 † | 12/2010 | Mamchur | |
| 2011/0071122 A1 † | 3/2011 | Mamchur | |
| 2011/0311592 A1 * | 12/2011 | Birbara | ..................... 424/400 |
| 2015/0196568 A1 † | 7/2015 | Mamchur | |

OTHER PUBLICATIONS

Sepiclear G4TM, Septic, Feb. 2014.*
Resplanta, safety datasheet, Jan. 2010.*
Olivatis 15; Technical Data Sheet; Medolla Cosmetic Speciality Ingredients; distributed by: CoastSouthwest.

\* cited by examiner
† cited by third party

*Primary Examiner* — Jean Cornet
(74) *Attorney, Agent, or Firm* — David G. Woodral; Scott R. Zingerman; Gable Gotwals

(57) ABSTRACT

The present disclosure refers to heptyl glucoside included, as a natural solubilizer and as a skin penetration enhancer, in transdermal pharmaceutical compositions. Heptyl glucoside is a natural alkyl glycoside and a hydrotrope that improves solubility of active pharmaceutical ingredients (APIs), thereby enhancing skin permeability to APIs. Transdermal pharmaceutical compositions including heptyl glucoside allow lower APIs dosage requirements. Heptyl glucoside can be combined with at least one API and suitable ingredients to formulate transdermal pharmaceutical compositions with improved skin permeability, thereby promoting percutaneous absorption of APIs. Transdermal pharmaceutical compositions including heptyl glucoside can be formulated in a plurality of dosage forms, such as, a liquid, cream, paste, gel, lotion, patch (e.g., matrix and reservoir), tape, film former (e.g., plaster), and the like.

9 Claims, No Drawings

USE OF HEPTYL GLUCOSIDE AS SKIN PENETRATION ENHANCER IN TRANSDERMAL PHARMACEUTICAL COMPOSITIONS

CROSS REFERENCE TO RELATED APPLICATIONS

N/A

BACKGROUND

Field of the Disclosure

The present disclosure relates generally to pharmaceutical compositions, and more particularly, to natural solubilizers and penetration enhancers that improve drug's permeability to the skin employed in transdermal pharmaceutical compositions for the delivery of active pharmaceutical ingredients (APIs).

Background Information

The delivery of active pharmaceutical ingredients (APIs) through a biological surface (e.g., skin tissue) is a well-recognized method of treatment for controlled drug delivery. Such APIs are delivered to the surface of the skin of a patient with transdermal delivery through the skin occurring thereafter.

Transdermal drug delivery is receiving increased attention because of the ability of an administration regime to provide a controlled route for the release of an API into the systemic circulation of the patient. The delivery of drugs using a transdermal methodology provides many benefits as compared to other delivery methods, such as, for example topical, oral, injection, and the like. Primarily, transdermal delivery is a comfortable, convenient and non-invasive way of administering drugs. Issues with other drug delivery methods include, for example, the variable rates of absorption of APIs in each metabolism encountered when using oral treatments, and other inherent inconveniences, such as, gastrointestinal irritation.

Transdermal delivery is a particularly advantageous delivery route. It is a non-invasive drug delivery method with the benefits of better patient compliance, less risk of infection, and lower cost than invasive procedures such as injection and implantation. Transdermal delivery also provides a much shorter onset time (e.g., the time from administration to therapeutic effect) than oral delivery does. Transdermal applications of APIs are simple and can be administered by a caregiver or the patient with minimal discomfort.

The lower solubility and relatively lower permeability of many APIs with diverse physicochemical characteristics can be improved using chemical enhancement means. Issues with most known chemical solubilizers and penetration enhancers include, for example, that they are often toxic, irritating, or allergenic. Improving APIs solubility may result in the decrease or elimination of penetration enhancers and thereby result in APIs becoming more bioavailable, and hence, more effective for a given dose. Accordingly, there is a need to provide improved API solubility, and improved skin permeation for use in transdermal pharmaceutical compositions.

SUMMARY

The present disclosure refers to heptyl glucoside employed as a natural solubilizer and as a skin penetration enhancer for use in transdermal pharmaceutical compositions. Heptyl glucoside is a natural alkyl glycoside and a hydrotrope that improves solubility of active pharmaceutical ingredients (APIs), thereby enhancing skin permeability to APIs. In some embodiments, heptyl glucoside is derived from a sugar (e.g., starch, obtained from corn or wheat) and an alcohol (e.g., heptanol, obtained from castor seeds).

In some embodiments, heptyl glucoside is: a 100% biobased non-ionic surfactant; a concentrated oil/water solubilizer; easily biodegradable; and free of ethoxylated oils. In these embodiments, heptyl glucoside enables the introduction of hydrophobic compounds into an aqueous medium. Further to these embodiments, heptyl glucoside allows a complete dissolution of the APIs, improves water solubility, and increases skin permeation. Additionally, heptyl glucoside solubilizes lipophilic compounds contained within aqueous media, such as, essential oils, perfumes, vitamin E, and the like. In these embodiments, heptyl glucoside is included within a transdermal pharmaceutical composition in amounts ranging from about 1% w/w to about 99% w/w.

In other embodiments, heptyl glucoside is combined with at least one API and suitable ingredients to formulate a transdermal pharmaceutical composition having improved skin permeability. In these embodiments, the transdermal pharmaceutical composition having improved skin permeability promotes transdermal absorption of the APIs. Further to these embodiments, heptyl glucoside is a transdermal absorption accelerator that promotes the transdermal absorption of APIs but does not alter the pharmaceutical composition. In these embodiments, heptyl glucoside promotes the delivery of APIs, thereby resulting in a higher percentage of bioavailability of the APIs to the patient. Further to these embodiments, the transdermal pharmaceutical compositions including heptyl glucoside comprise APIs in amounts ranging from about 0.5% w/w to about 30% w/w.

In some embodiments, the transdermal pharmaceutical compositions including heptyl glucoside comprise at least one additional component, such as, surface active agents, dispersing agents, coloring agents, preservatives, solvents, emulsifying agents, pH regulators, and antioxidants, among others. In these embodiments, the transdermal pharmaceutical compositions including heptyl glucoside comprise one or more of each of the aforementioned additional components as well as one or more of each type of the additional components. Further to these embodiments, transdermal pharmaceutical compositions formulated with heptyl glucoside include a plurality of dosage forms.

In other embodiments, the subject to be treated with transdermal pharmaceutical compositions is generally a mammal, and preferably a human being. In these embodiments, when the heptyl glucoside is employed within the transdermal pharmaceutical compositions, low doses of APIs are required. This contrasts with current popular topical treatment options, which require high doses of APIs to deliver a few milligrams of said APIs into the bloodstream.

In some embodiments, the doses required depend on the type of APIs included within the transdermal pharmaceutical compositions comprising heptyl glucoside. In these embodiments, the transdermal pharmaceutical compositions are administered in suitable doses as directed by a physician.

Numerous other aspects, features, and benefits of the present disclosure may be made apparent from the following detailed description.

DETAILED DESCRIPTION

Definitions

As used here, the following terms have the following definitions:

"Active Pharmaceutical Ingredients (APIs)" refer to chemical compounds that induce a desired effect, and include agents that are therapeutically or prophylactically effective.

"Biobased" refers to materials or products that are composed in whole, or in significant part, of biological products or renewable agricultural materials, or forestry materials.

"Permeation Enhancer" or, equivalently, "Penetration Enhancer" refers to a substance used to modify, generally to increase, the rate of permeation through skin or other body tissue of one or more substances (e.g., APIs) in a formulation.

"Transdermal drug delivery" refers to administration of a drug to the skin surface of an individual so that the drug passes through the skin tissue and into the subject's blood stream, thereby providing a systemic effect.

DESCRIPTION OF THE DISCLOSURE

The present disclosure refers to heptyl glucoside employed as a natural solubilizer and as a skin penetration enhancer for use in transdermal pharmaceutical compositions. Heptyl glucoside is a natural alkyl glycoside and a hydrotrope that improves solubility of active pharmaceutical ingredients (APIs), thereby enhancing skin permeability to APIs. In some embodiments, heptyl glucoside is derived from a sugar (e.g., starch, obtained from corn or wheat) and an alcohol (e.g., heptanol, obtained from castor seeds).

In these embodiments, heptyl glucoside is expressed by the following formula:

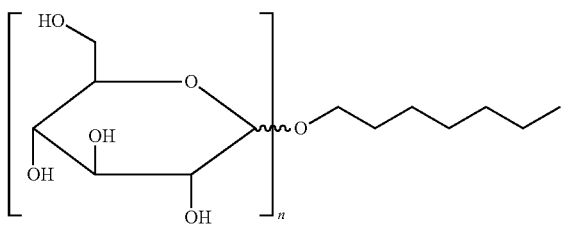

In some embodiments, heptyl glucoside is: a 100% biobased non-ionic surfactant; a concentrated oil/water solubilizer; easily biodegradable; and free of ethoxylated oils. In these embodiments, heptyl glucoside enables the introduction of hydrophobic compounds into an aqueous medium. Further to these embodiments, heptyl glucoside allows a complete dissolution of the APIs, improves water solubility, and increases skin permeation. Additionally, heptyl glucoside solubilizes lipophilic compounds contained within aqueous media, such as, essential oils, perfumes, vitamin E, and the like. In these embodiments, heptyl glucoside is included within a transdermal pharmaceutical composition in amounts ranging from about 1% w/w to about 99% w/w.

In other embodiments, heptyl glucoside is combined with at least one API and suitable ingredients to formulate a transdermal pharmaceutical composition having improved skin permeability. In these embodiments, the transdermal pharmaceutical composition having improved skin permeability promotes transdermal absorption of the APIs. Further to these embodiments, heptyl glucoside is a transdermal absorption accelerator that promotes the transdermal absorption of APIs but does not alter the pharmaceutical composition. In these embodiments, heptyl glucoside promotes the delivery of APIs, thereby resulting in a higher percentage of bioavailability of the APIs to the patient.

In some embodiments, APIs are selected from non-steroidal anti-inflammatory drugs, steroidal anti-inflammatory drugs, adrenergic receptor agonists, α-adrenergic receptor blockers, β-adrenergic receptor blockers, calcium antagonists, angiotensin converting enzyme inhibitors, angiotensin II receptor antagonists medicine, anti-arrhythmic drugs, diuretics, hyperlipidemia treatment, peripheral vasodilators, inotropic agents, angina treatment, coronary vasodilator, anti-clotting drug, psychotropic drugs, sleeping pills, anesthetics, anti-vomiting agents, antibiotics, such as quinolone antibiotic medicine, oral hypoglycemic agents, hormone medicine, Parkinson's disease treatment, erectile dysfunction treatment drugs, antihistamines, bone resorption inhibitors, malignant tumor treatment, ephalosporin antibiotics, and vitamins, among others. In these embodiments, the transdermal pharmaceutical compositions including heptyl glucoside comprise APIs in amounts ranging from about 0.5% w/w to about 30% w/w.

The following

| Ingredients | Percentage | Commercial name |
|---|---|---|
| Estriol | 1% | |
| Heptyl Glucoside | 20% | Sepiclear |
| QS Olive Oil Glycereth-8 Esters | 79% | Olivatis 15 |

| Ingredients | Percentage | Comercial name |
|---|---|---|
| Estradiol | 1% | |
| Heptyl Glucoside | 20% | Sepiclear |
| QS Olive Oil Glycereth-8 Esters | 79% | Olivatis 15 |

In an embodiment of the present invention, the use of heptyl glucoside more completely solubilizes an introduced API and/or hormone(s) when the heptyl glucoside is at about 20% w/w. Lower and/or higher concentrations of heptyl glucoside does not permit the complete solubilization of an introduced API and/or hormone(s).

In other embodiments, the transdermal pharmaceutical compositions including heptyl glucoside comprise at least one additional component, such as, surface active agents, dispersing agents, coloring agents, preservatives, solvents, emulsifying agents, pH regulators, and antioxidants, among others. In these embodiments, the transdermal pharmaceutical compositions including heptyl glucoside comprise one or more of each of the aforementioned additional components as well as one or more of each type of the additional components.

In other embodiments, the transdermal pharmaceutical compositions formulated with heptyl glucoside include a plurality of dosage forms, such as a liquid, cream, paste, gel, lotion, patch (e.g., matrix and reservoir), tape, film former (e.g., plaster, etc.), and the like.

In some embodiments, the subject to be treated with transdermal pharmaceutical compositions is generally a mammal, and preferably a human being. In these embodiments, when the heptyl glucoside is employed within the transdermal pharmaceutical compositions, low doses of APIs are required. This contrasts with current popular topical treatment options, which require high doses of APIs to deliver a few milligrams of said APIs into the bloodstream.

In other embodiments, the doses required depend on the type of APIs included within the transdermal pharmaceutical compositions comprising heptyl glucoside. In these embodiments, the transdermal pharmaceutical compositions are administered in suitable doses as directed by a physician.

While various embodiments of the present disclosure have been described above, it should be understood that they have been presented by way of example only, and not limitation. Numerous changes to the disclosed embodiments can be made in accordance with the disclosure herein without departing from the spirit or scope of the disclosure. Thus, the breadth and scope of the present disclosure should not be limited by any of the above described embodiments.

Rather, the scope of the disclosure should be defined in accordance with the following claims and their equivalents.

Although the present disclosure has been illustrated and described with respect to one or more implementations, equivalent alterations and modifications can occur to others skilled in the art upon the reading and understanding of this specification and the drawings. In addition, while a particular feature of the disclosure may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A composition to be used for skin permeation, the composition comprising a combination of: 20% w/w heptyl glucoside; 1-10% w/w of a steroidal hormone; and an olive oil ester, wherein the heptyl glucoside is used as a natural solubilizer and as a skin permeation enhancer.

2. The composition of claim 1, wherein the steroidal hormone is present at 1% w/w.

3. The composition of claim 1, wherein the steroidal hormone is estradiol.

4. The composition of claim 1, wherein the steroidal hormone is estriol.

5. The composition of claim 1, wherein the oil ester is present at 79% w/w.

6. The composition of claim 1, wherein the oil ester is Olive Oil Glycereth-8 Ester.

7. A composition to be used for skin permeation, the composition comprising a combination of: 20% w/w heptyl glucoside; 1-10% w/w of a steroidal hormone; and an olive oil glycereth-8 ester, wherein the heptyl glucoside is used as a natural solubilizer and as a skin permeation enhancer.

8. The composition of claim 7, wherein the steroidal hormone is present at 1% w/w.

9. The composition of claim 7, wherein the composition is in a form selected from the group consisting of a liquid, cream, paste, gel, lotion, patch, tape, film former, and combinations thereof.

* * * * *